United States Patent
Mikus et al.

[11] Patent Number: 6,074,412
[45] Date of Patent: Jun. 13, 2000

[54] CRYOPROBE

[75] Inventors: Paul W. Mikus; Gregory L. Kelly; Ralph K. Brady, all of Irvine, Calif.

[73] Assignee: Endocare, Inc., Irvine, Calif.

[21] Appl. No.: 09/143,925

[22] Filed: Aug. 29, 1998

Related U.S. Application Data

[63] Continuation of application No. 08/685,233, Jul. 23, 1996, Pat. No. 5,800,487.

[51] Int. Cl.[7] .................................................. A61F 7/00
[52] U.S. Cl. .............................. 607/105; 606/20; 606/21; 606/22; 606/24
[58] Field of Search ................... 606/20–26; 62/51.2, 62/293; 607/105, 107

[56] References Cited

U.S. PATENT DOCUMENTS

| | | | |
|---|---|---|---|
| 3,398,738 | 8/1968 | Lamb . | |
| 3,658,066 | 4/1972 | Saidi et al. . | |
| 3,800,552 | 4/1974 | Sollami et al. | 62/293 |
| 3,913,581 | 10/1975 | Ritson et al. . | |
| 4,028,907 | 6/1977 | Herrington | 62/222 |
| 4,063,560 | 12/1977 | Thomas et al. . | |
| 4,306,568 | 12/1981 | Torre . | |
| 4,486,935 | 12/1984 | Albagnac | 62/514 |
| 4,946,460 | 8/1990 | Merry et al. | 606/24 |
| 5,018,713 | 5/1991 | Varney | 606/23 |
| 5,077,979 | 1/1992 | Skertic | 62/51.2 |
| 5,108,390 | 4/1992 | Potocky et al. | 606/21 |
| 5,150,579 | 9/1992 | Hingst | 62/51.2 |
| 5,388,415 | 2/1995 | Glinka et al. | 62/51.2 |
| 5,452,582 | 9/1995 | Longsworth | 62/51.2 |
| 5,522,870 | 6/1996 | Ben-Zion | 607/104 |
| 5,993,444 | 11/1999 | Ammar et al. | 606/21 |

FOREIGN PATENT DOCUMENTS

| | | |
|---|---|---|
| 0 608 927 | 8/1994 | European Pat. Off. . |
| 1217377 | 6/1984 | U.S.S.R. ................ A61B 17/36 |

OTHER PUBLICATIONS

Walker & Bingham, Low Capacity Cryogenic Refrigeration, p. 67 at seq. (1994).

Onik et al., Transrectal Ultrasound–Guided Percutaneous Radial Cryosurgical Ablation of the Prostate, 72 Cancer 1291 (1993).

Onik et al, Percutaneous Prostate Cryoablation (1995).

Onik, Ultrasound–Guided Cryosurgery, Scientific American at 62 (Jan. 1986).

*Primary Examiner*—Linda C. M. Dvorak
*Assistant Examiner*—R. Kearney
*Attorney, Agent, or Firm*—K. David Crockett, Esq.; Crockett & Crockett

[57] ABSTRACT

Cryocoolers for use in cryosurgery and other applications comprising dual finned tube helical coil heat exchangers. The size and shape of iceballs created by the probes is controlled by the location of the gas outlets within the cryocooler outer sheath.

7 Claims, 16 Drawing Sheets

CRYOPROBE

This application is a continuation of U.S. application Ser. No. 08/685,233 filed Jul. 23, 1996, now U.S. Pat. No. 5,800,487 issued Sep. 1, 1998.

FIELD OF THE INVENTION

This invention relates to cryocoolers, and to cryoprobes for use in cryosurgery.

BACKGROUND OF THE INVENTION

Cryosurgical probes are used to treat a variety of diseases. The cryosurgical probes quickly freeze diseased body tissue, causing the tissue to die after which it will be absorbed by the body or expelled by the body or sloughed off. Cryothermal treatment is currently used to treat prostate cancer and benign prostate disease, breast tumors and breast cancer, liver tumors and cancer, glaucoma and other eye diseases. Cryosurgery is also proposed for the treatment of a number of other diseases.

The use of cryosurgical probes for cryoablation of prostate is described in Onik, *Ultrasound-Guided Cryosurgery,* Scientific American at 62 (January 1996) and Onik, Cohen, et al., *Transrectal Ultrasound-Guided Percutaneous Radial Cryosurgical Ablation Of The Prostate,* 72 Cancer 1291 (1993). In this procedure, generally referred to as cryoablation of the prostate, several cryosurgical probes are inserted through the skin in the perineal area (between the scrotum and the anus) which provides the easiest access to the prostate. The probes are pushed into the prostate gland through previously place cannulas. Placement of the probes within the prostate gland is visualized with an ultrasound imaging probe placed in the rectum. The probes are quickly cooled to temperatures typically below –120 C. The prostate tissue is killed by the freezing, and any tumor or cancer within the prostate is also killed. The body will absorb some of the dead tissue over a period of several weeks. Other necrosed tissue may slough off through the urethra. The urethra, bladder neck sphincter and external sphincter are protected from freezing by a warming catheter placed in the urethra and continuously flushed with warm saline to keep the urethra from freezing.

Rapid re-warming of cryosurgical probes is desired. cryosurgical probes are warmed to promote rapid thawing of the prostate, and upon thawing the prostate is frozen once again in a second cooling cycle. The probes cannot be removed from frozen tissue because the frozen tissue adheres to the probe. Forcible removal of a probe which is frozen to surrounding body tissue leads to extensive trauma. Thus many cryosurgical probes provide mechanisms for warming the cryosurgical probe with gas flow, condensation, electrical heating, etc.

A variety of cryosurgical instruments, variously referred to as cryoprobes, cryosurgical ablation devices, and cryostats and cryocoolers, have been available for cryosurgery. The preferred device uses Joule-Thomson cooling in devices known as Joule-Thomson cryostats. These devices take advantage of the fact that most gases, when rapidly expanded, become extremely cold. In these devices, a high pressure gas such as argon or nitrogen is expanded through a nozzle inside a small cylindrical sheath made of steel, and the Joule-Thomson expansion cools the steel sheath to sub-freezing cryogenic temperature very rapidly.

An exemplary device is illustrated in Sollami, Cryogenic Surgical Instrument, U.S. Pat. No. 3,800,552 (Apr. 2, 1974). Sollami shows a basic Joule-Thomson probe with a sheath made of metal, a fin-tube helical gas supply line leading into a Joule Thomson nozzle which directs expanding gas into the probe. Expanded gas is exhausted over the fin-tube helical gas supply line, and pre-cools incoming high pressure gas. For this reason, the coiled supply line is referred to as a heat exchanger, and is beneficial because, by pre-cooling incoming gas, it allows the probe to obtain lower temperatures.

Ben-Zion, Fast Changing Heating and Cooling Device and Method, U.S. Pat. No. 5,522,870 (Jun. 4, 1996) applies the general concepts of Joule-Thomson devices to a device which is used first to freeze tissue and then to thaw the tissue with a heating cycle. Nitrogen is supplied to a Joule-Thomson nozzle for the cooling cycle, and helium is supplied to the same Joule-Thomson nozzle for the warming cycle. Preheating of the helium is presented as an essential part of the invention, necessary to provide warming to a sufficiently high temperature.

A Joule-Thomson cryostat for use as a gas tester is illustrated in Glinka, System for a Cooler and Gas Purity Tester, U.S. Pat. No. 5,388,415 (Feb. 14, 1995). Glinka also discloses use of the by-pass from the Joule-Thomson Nozzle to allow for cleaning the supply line, and also mentions that the high flow of gas in the by-pass mode will warm the probe. This is referred to as mass flow warming, because the warming effect is accomplished purely by conduction and convection of heat to the fluid mass flowing through the probe.

Various cryocoolers use mass flow warming, flushed backwards through the probe, to warm the probe after a cooling cycle. Lamb, Refrigerated Surgical Probe, U.S. Pat. No. 3,913,581 (Aug. 27, 1968) is one such probe, and includes a supply line for high pressure gas to a Joule-Thomson expansion nozzle and a second supply line for the same gas to be supplied without passing through a Joule-Thomson nozzle, thus warming the catheter with mass flow. Longsworth, Cryoprobe, U.S. Pat. No. 5,452,582 (Sep. 26, 1995) discloses a cryoprobe which uses the typical fin-tube helical coil heat exchanger in the high pressure gas supply line to the Joule-Thomson nozzle. The Longsworth cryoprobe has a second inlet in the probe for a warming fluid, and accomplishes warming with mass flow of gas supplied at about 100 psi. The heat exchanger, capillary tube and second inlet tube appear to be identical to the cryostats previously sold by Carleton Technologies, Inc. of Orchard Park, N.Y.

Each of the above mentioned cryosurgical probes builds upon prior art which clearly establishes the use of Joule-Thomson cryocoolers, heat exchangers, thermocouples, and other elements of cryocoolers. Walker, *Miniature Refrigerators for Cryogenic Sensor and Cold Electronics* (1989) (Chapter 2) and Walker & gingham, Low *Capacity Cryogenic Refrigeration,* pp. 67 et seq. (1994) show the basic construction of Joule-Thomson cryocoolers including all of these elements. The Giaque-Hampson heat exchanger, characterized by coiled finned-tube, transverse flow recuperative heat exchanger is typical of cryocoolers. The open mandrel around which the finned tube coil is placed is also typical of cryocoolers.

Cryosurgical probes may be used, as mentioned above, to treat diseases of the prostate, liver, and breast, and they have gynecological applications as well. The cryosurgical probes form iceballs which freeze disease tissue. Each application has a preferred shape of iceball, which, if capable of production, would allow cryoablation of the diseases tissue without undue destruction of surrounding healthy tissue. For example, prostate cryoablation optimally destroys the lobes of the prostate, while leaving the surrounding neurovascular bundles, bladder neck sphincter and external sphincter undamaged. The prostate is wider at the base and narrow at the apex. A pear or fig shaped ice ball is best for this application. Breast tumors tend to be small and spherical, and spherical iceballs will be optimal to destroy the tumors without destroying surrounding breast tissue. Liver tumors may be larger and of a variety of shapes, including spherical, olive shaped, hot dog shaped or irregularly shaped, and may require more elongated iceballs, larger iceballs, and iceballs of various shapes.

SUMMARY

The heat exchanger comprises a Giaque-Hampson heat exchanger with finned tube gas supply line coiled around a mandrel. After expansion in the tip of the cryoprobe, the gas flows over the coils and exhausts out the proximal end of the probe. The flow of exhaust gas over the heat exchanger coils is controlled by placement of a flow directing sheath placed in different longitudinal areas of the heat exchanger. To create spherical iceballs, the thermal barrier is placed over the entire length of the heat exchanger coil. To create pear shaped iceballs, the flow directing sheath is place over the proximal portion of the coil, but not over the distal portion of the coil. For an elongate cylindrical iceball, which we call hot dog shaped, the flow directing sheath is placed over the proximal end of the heat exchanger coil, but not over the distal end of the coil, and the nozzle is placed proximally from the cryoprobe tip. Alternative embodiments include variation of the length of the straight supply tube extending distally from the helical coil heat exchanger, and variation of the distance of the Joule-Thomson nozzle from the distal tip of the probe.

These shapes are desired for the several shapes of tissues that are subject to cryosurgical treatment. The olive-shaped and pear-shaped iceballs are useful for prostate treatment, as they permit creation of the optimal iceball within the prostate. The spherical iceball is desired for treatment of breast tumors, which tend to be spherical. The oblong iceball is desired for treatment of liver tumors, which tend to be oblong. Of course, the correspondence of the shapes to the anatomical site is not a hard and fast rule, and each shape of iceball will be useful in any area of the body wherein a tumor or other condition indicates use of a particular shape.

Parallel finned tubes are used in one embodiment to create a dual helix design. In this embodiment, two parallel gas supply lines are used, and they are wound in parallel around the mandrel. The nozzles tips may be located equidistant from the tip of the probe for a spherical iceball, and they may be offset, with one nozzle placed distally of the other to create an oblong iceball. Both of the dual coils can be used to supply high pressure gas which cools upon expansion (nitrogen, argon, $NO_2$, $CO_2$, etc.), so that both coils are used for cooling. One coil can be used for cooling gas while the other coil is used for the supply of a high pressure gas which heats upon expansion (hydrogen, helium, and neon).

Separate cooling and heating Joule-Thomson nozzles are used in an embodiment wherein the heating gas is supplied through the mandrel. In this embodiment, the heating gas supply is not subject to heat exchange with the exhausting heating gas to create a higher initial heating rate. To permit complete control of both heating and cooling, the several cryoprobes are supplied with gas through a dual manifold which allows for independently warming each probe. This allows removal of individual probes in case the doctor performing the cryosurgery decides that a cryoprobe must be moved after it has formed an iceball. It also allows protective warming for nearby anatomical structures.

DETAILED DESCRIPTION OF THE INVENTION

Figure 1:
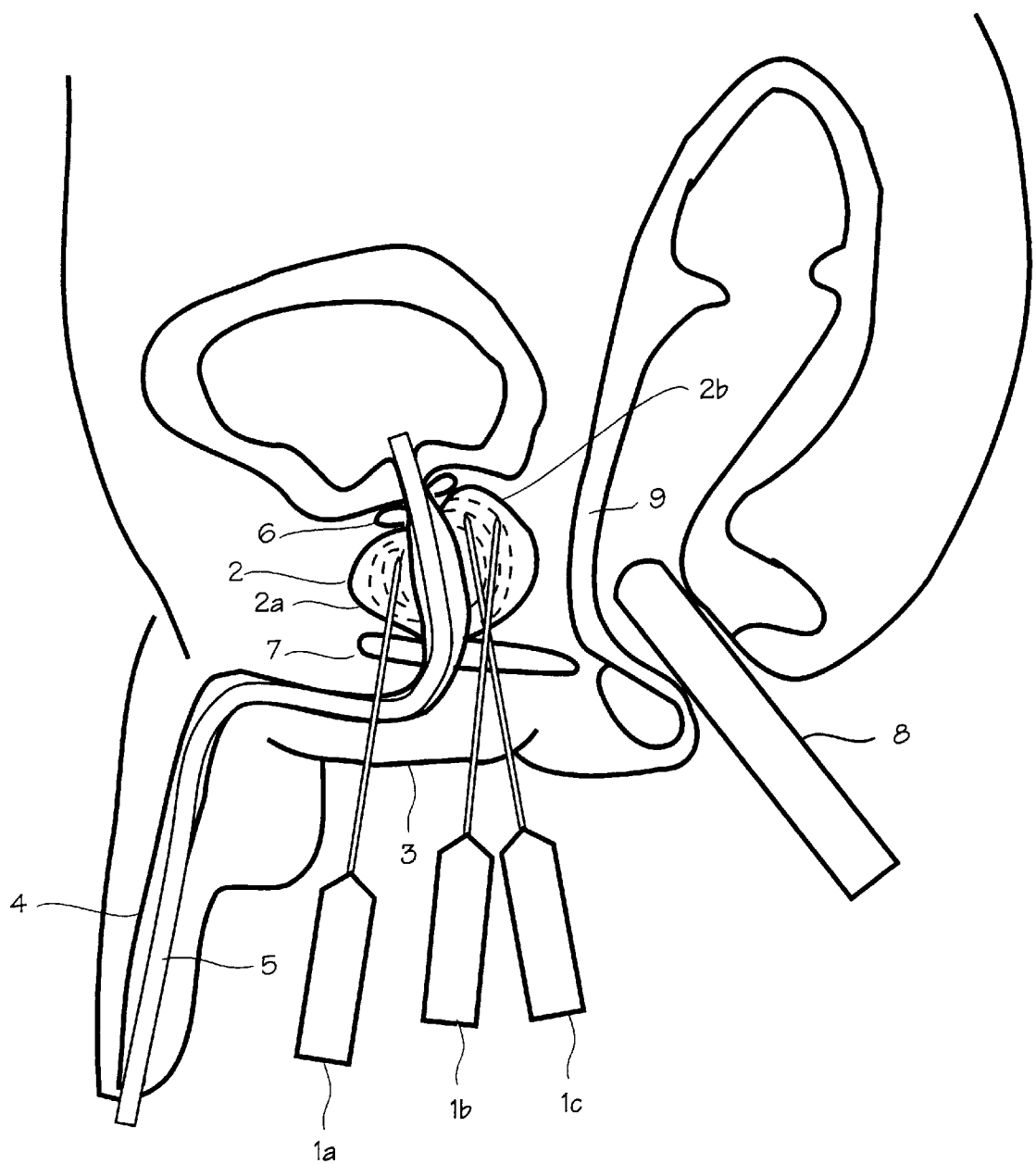
FIG. 1 is a schematic drawing of the probes of the present invention in use in the transperineal cryosurgical ablation of the prostate.

FIG. 1 shows one of the basic operations for which the cryoprobes are designed. Several probes 1a, 1b, and 1c are shown inserted in the prostate 2. All three probes are inserted through the perineal region 3 between the scrotum and the anus. Probe 1a is shown inserted into the anterior lobe 2b of the prostate, and Probes 1b and 1o are shown inserted into the posterior lobe 2a, which is larger than the anterior lobe. The probes are placed within the prostate according to procedures well known in the art, and a suitable procedure is described in step-by-step detail in Onik, et al., *Percutaneous Prostate Cryoablation*, (1995) at pages 108–112 and Onik, *Ultrasound-Guided Cryosurgery Scientific American* at 62. (January 1996). The urethra 4 which passes through the prostate is one of the anatomic structures that usually should not be frozen during this surgery. Accordingly, the urethra is protected and kept warm with the urethral warming catheter 5. The bladder neck sphincter 6 and the external sphincter are also structures that should be protected from freezing, and these are protected from freezing by the warming catheter. Neurovascular bundles on the right and left of the prostate should also be protected from freezing. Transrectal probe 8 is inserted into the rectum 9 in order to visualize the placement of the probes and the growth of the iceballs formed by the cryoprobes.

Figure 2:
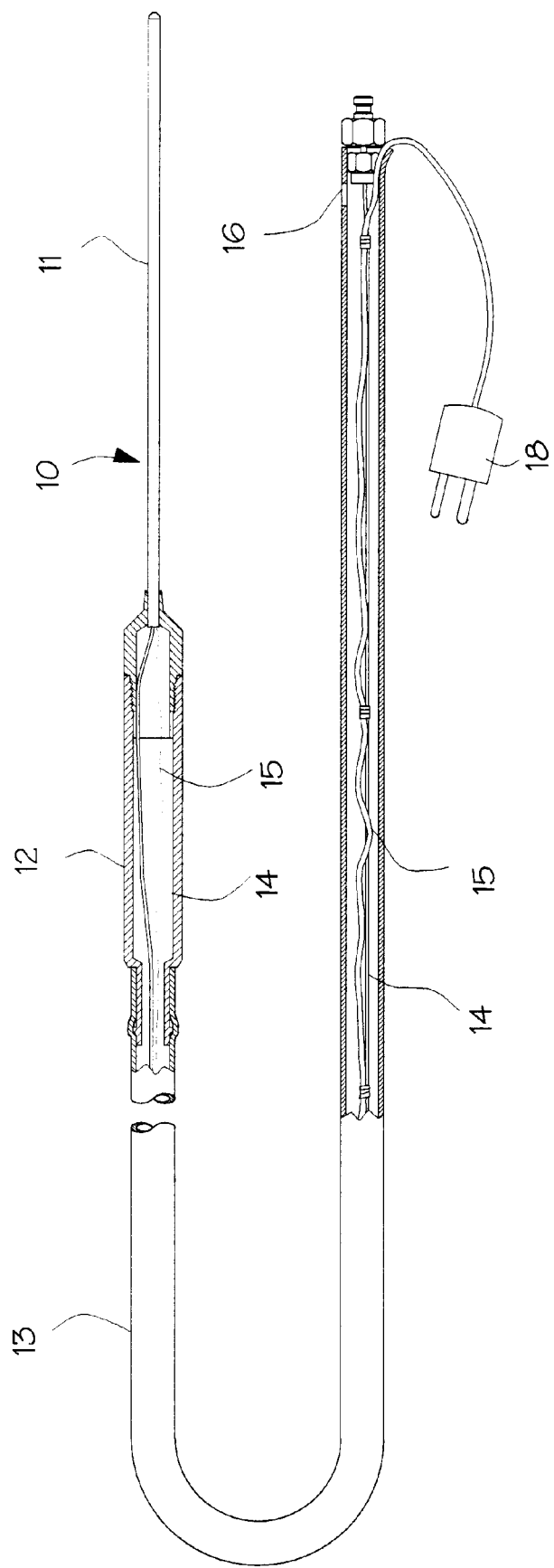
FIG. 2 is a view of the cryosurgical probe including the tubing connecting the probe to gas supplies.

FIG. 2 shows the entire cryosurgical probe assembly. The cryoprobe 1 includes a cryocooler 10 about 25 cm (10 inches) long and 3.5 mm (0.134 in.) in diameter. These sizes are convenient and preferred for cryoprobes intended for prostate use, and may vary widely. The probe outer sheath 11 houses the cryostat described in detail below. A handle 12 of convenient size is provided. The flexible tube 13 houses gas supply lines 14 and thermocouple electrical wiring 15, and has a vent 16 for exhaust gas. The gas supply line is connected to a high pressure gas supply through high pressure fitting 17. The thermocouple wire is connected to the control system through electrical connector 15.

Figure 3:
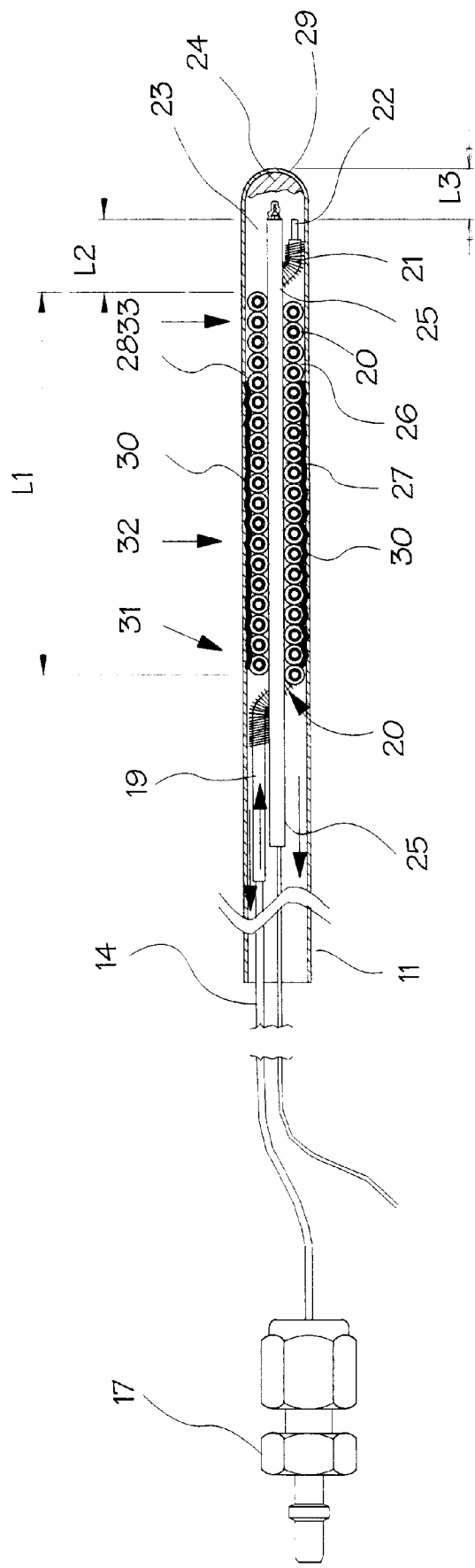
FIG. 3 is a cross section of the cryosurgical probe adapted to provide a pear shaped iceball.
Figure 4:
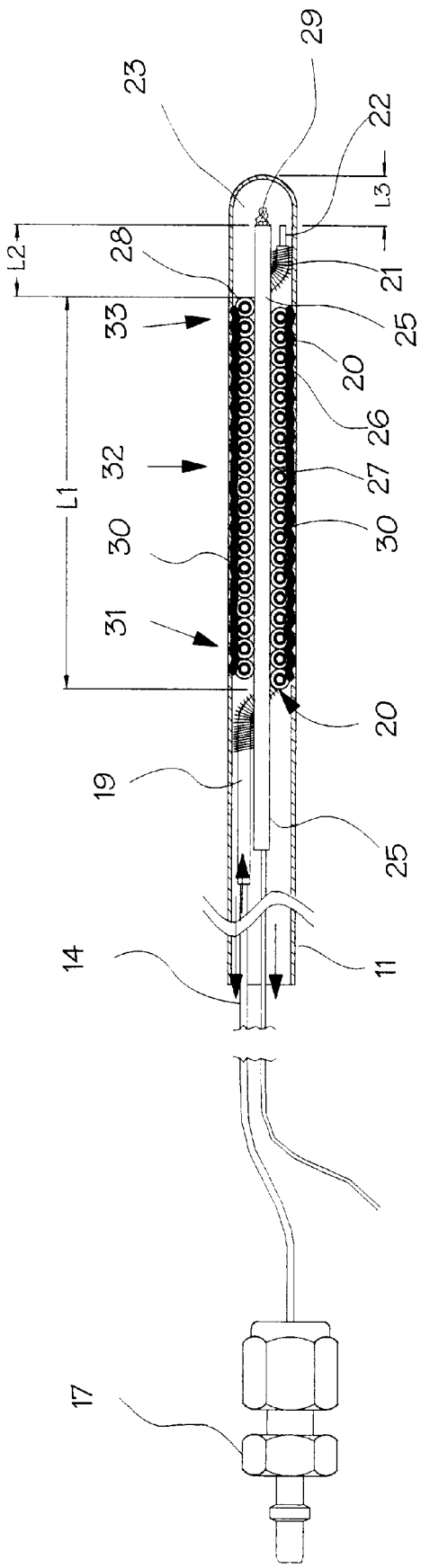
FIG. 4 is a cross section of the cryosurgical probe adapted to provide a oblong or olive-shaped iceball.

The details of the cryostat used in the cryosurgical probe are illustrated in FIGS. 3 through 6. FIG. 3 shows the basic embodiment of the cryosurgical probe. The high pressure gas supply line 14 connects to the proximal extension 19 of the finned tube coiled heat exchanger 20. The heat exchanger extends longitudinally through the outer sheath 11 and connects to the cooling fluid outlet comprising distal extension 21 which open through Joule-Thomson nozzle 22 into expansion chamber 23. The expansion chamber size and shape is controlled in part by the inner surface of the distal end plug and thermal barrier 24 which seals the outer sheath 11 and closes the distal end of the sheath. The outer sheath is made of thermally conductive material such as stainless steel. The end plug may take many shapes but preferably has a rounded outer contour and a convex inner surface as shown. The end plug may be made of stainless steel, or it may be made of tantalum, titanium, ceramic or other relatively insulating material to inhibit heat transfer from the tip of the probe. The heat exchanger is coiled around mandrel 25. The distal endpoint of the mandrel and the distal endpoint of the Joule-Thomson nozzle are equidistant from the end plug. In between each winding of the heat exchanger, gaps 26 are formed between the coil and the outer sheath, and gaps 27 are formed between the coil and the mandrel. This construction is known as a Giaque-Hampson heat exchanger.

The heat exchanger, which is an integral part of the high pressure gas pathway, is made with finned tubing, with numerous fins 28 throughout its length. The finned tubing is approximately 30 cm (12 inches) long and 0.75 mm (0.030 in.) in outer diameter and the fins are approximately 1 mm (0.0437 in.) in diameter. The finned tube coil is wrapped around the mandrel for 18 turns or so. The fins are stripped from the proximal extension for a length sufficient to allow insertion of the finned tubing into high pressure line 14 and soldering of the high pressure line to the finned tube. The mandrel is 0.75 mm. (032 in.) in outer diameter and 10 cm (3.75 in.) long. The Joule-Thomson nozzle is approximately 1.5 mm (0.0625 in.), with an internal diameter of 0.2 mm (0.008 in.). At the distal tip of the mandrel is a thermocouple 29 which is used to measure and monitor the temperature inside the cryosurgical probe.

Control of the iceball shape is accomplished primarily with the flow directing sheath 30. The flow directing sheath shown in FIG. 3 is conveniently made of a heat shrink tube 3.25 cm (1.5 in.) long and 0.03 mm (1.75 mils) thick. The flow directing sheath surrounds the heat exchanger coil and is generally coaxially disposed about the heat exchanger. In the preferred embodiment, the flow directing sheath protrudes radially into the interstitial ridges between the windings or turns of the heat exchanger coil, as illustrated in FIG. 3 and the other figures illustrating the flow directing sheath. The flow directing sheath lengthens the gas flow path and forces gas to flow past the fins of the finned tube rather than flowing through the interstitial ridges between the turns of the helix. The sheath 30 also serves as a thermal barrier, isolating and/or insulating the outer sheath 11 from the cold expanded gas flowing over the finned tube heat exchanger. This thermal barrier can be customized during manufacture to control the heat exchange characteristics of the probe and thereby control the shape of the iceball created by the probe. The length and number of windings covered by the flow directing sheath/thermal barrier is predetermined based on the desired iceball shape for which each probe is made.

Fluid flow through the cryosurgical probe is as follows. High pressure fluid, preferably gaseous nitrogen or argon, and preferably at a pressure of about 3000 psi, is supplied to the assembly through high pressure fitting 17, flows through gas supply line 14, into heat exchanger 20 and through cooling fluid outlet 21 and Joule-Thomson nozzle 22. The high pressure gas expands within the expansion chamber and cools to cryogenic temperatures. Condensation of the gas is preferably avoided but can be tolerated. After expanding, the gas is at lower pressure and exhausts over the exhaust gas pathway which includes flow over outside of the coils of the heat exchanger 20. Because it is now cold, it cools the gas flowing inside the coils. This makes cooling more efficient and allows use of less gas. While flowing over the outside of the finned tube, the gas is directed away from the inside of the outer sheath 11 thus preventing any significant heat exchange with the outer sheath. After passing through the heat exchanger, the exhaust gas flows through the remainder of the exhaust gas pathway which includes the flexible tube and the vent 16 which vents the exhaust gas to atmosphere.

Various modifications of the flow directing sheath 30 allow creation of various iceball shapes. For convenience of reference, we refer three longitudinal segments of the helical coils as distal segment, central segment, and proximal segment. In FIG. 3, the flow directing sheath covers the proximal portion 31 and central portion 32 of the heat exchanger, and the distal portion 33 of the heat exchanger is left uncovered. The distance L3 between the Joule-Thomson nozzle and the end of the heat exchange chamber is approximately 5 mm (0.2 in.). The length L2 of the distal extension 21 of the heat exchanger is approximately 7.5 mm (0.30 in.). The length of the heat exchanger coil L1 is approximately 5 cm (2 in.). Operation of this cryosurgical probe within the body will create an ice ball having a pear shape. FIG. 3 also includes a thermal insulating end plug made of a materiel that is less thermally conductive than the stainless steel outer sheath in order to block heat transfer at the distal tip of the probe and thereby promote a flatter bottom for the pear shaped iceball.

Figure 5:
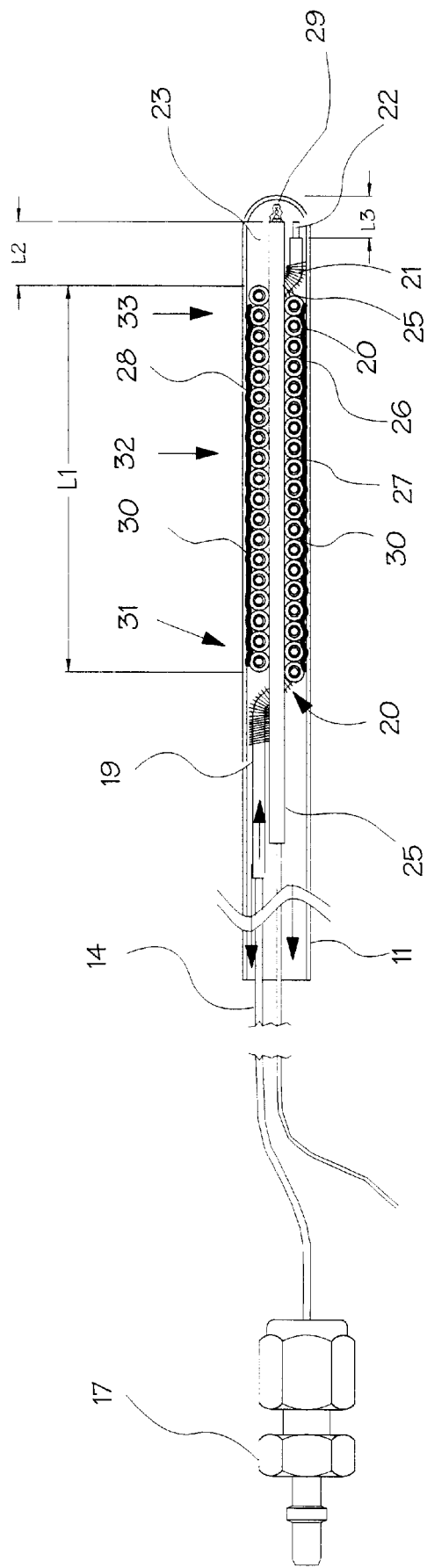
FIG. 5 is a cross section of the cryosurgical probe adapted to provide a spherical iceball.

In FIG. 5, the flow directing sheath is applied over substantially the entire length of the heat exchanger coil. The distance L3 between the Joule-Thomson nozzle and the end of the heat exchange chamber is approximately 5 mm (0.2 in.). The length L2 of the distal extension 21 of the heat exchanger is approximately 8 mm (0.3 in.). Operation of this cryosurgical probe within the body creates an iceball with a olive shape. In FIG. 5, the flow directing sheath is applied over substantially the entire length of the heat exchanger coil. The distance L3 between the Joule-Thomson nozzle and the end of the heat exchange chamber is approximately 2.5 mm (0.1 in.), significantly shorter than that shown for FIG. 4a. The length L2 of the distal extension 21 of the heat exchanger is approximately 5 mm (0.2 in.). Operation of this cryosurgical probe within the body creates an iceball with a olive shape.

Figure 6:
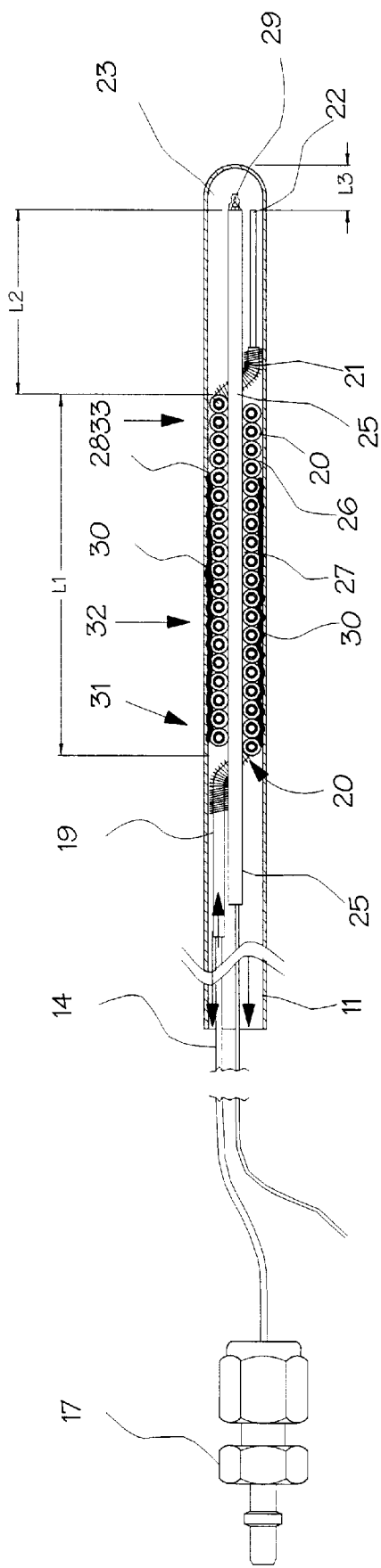
FIG. 6 is a cross section of the cryosurgical probe adapted to provide cylindrical iceball.

In FIG. 6, the flow directing sheath covers only the proximal portion of the helical coil. The distance L3 between the Joule-Thomson nozzle and the end of the heat exchange chamber is significantly longer that that shown in FIG. 5, approximately 5 mm (0.2 in.). The length L2 of the distal extension 21 of the heat exchanger is approximately 12.5 mm (0.6 in.). Operation of this cryosurgical probe within the body will create an ice ball having a hot dog shape.

Figure 7:
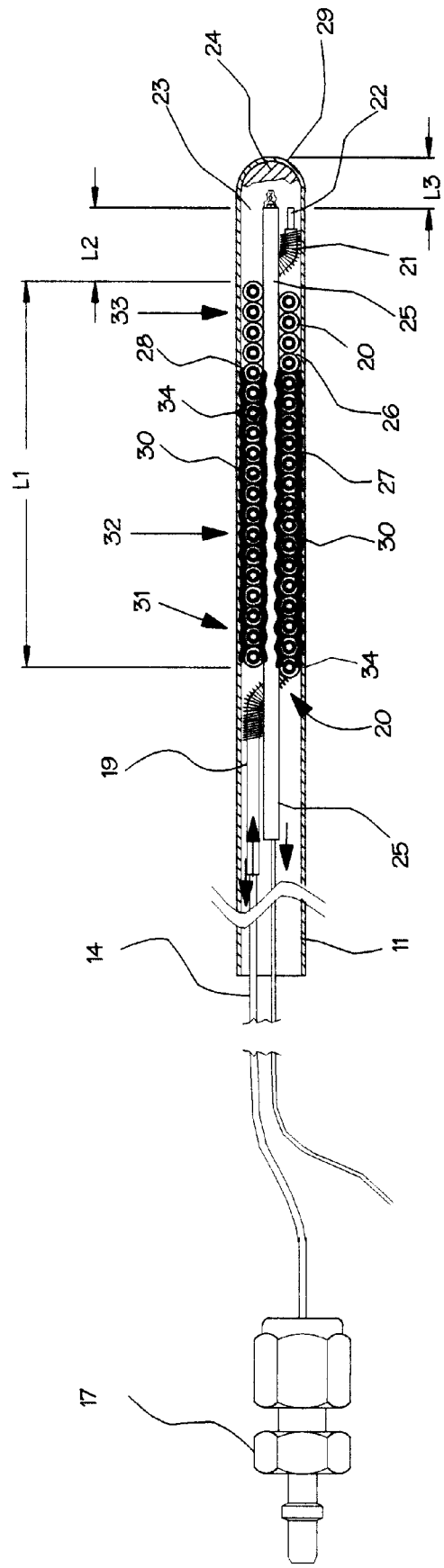
FIG. 7 is a cross section of the cryosurgical probe with parallel fin tubing and flow directing sheaths located inside and outside the heat exchanger coil.

Illustrated in FIG. 7 is an embodiment wherein the flow directing sheath is augmented with a second flow directing sheath 34 placed coaxially between the heat exchanger coils and the mandrel. The second flow directing sheath can be made with impressible material such as teflon, or may be integrally formed with the mandril. The inside sheath blocks flow through the gaps between the coils and forces all gas flow to pass the fins, thus promoting heat transfer. Thus it can be appreciated that the sheaths serve to block gas flow from flowing through the gaps between the windings and promotes more efficient heat exchange, a function previously accomplished by threads wrapped in the gaps, in parallel with the coils.

Figure 8:
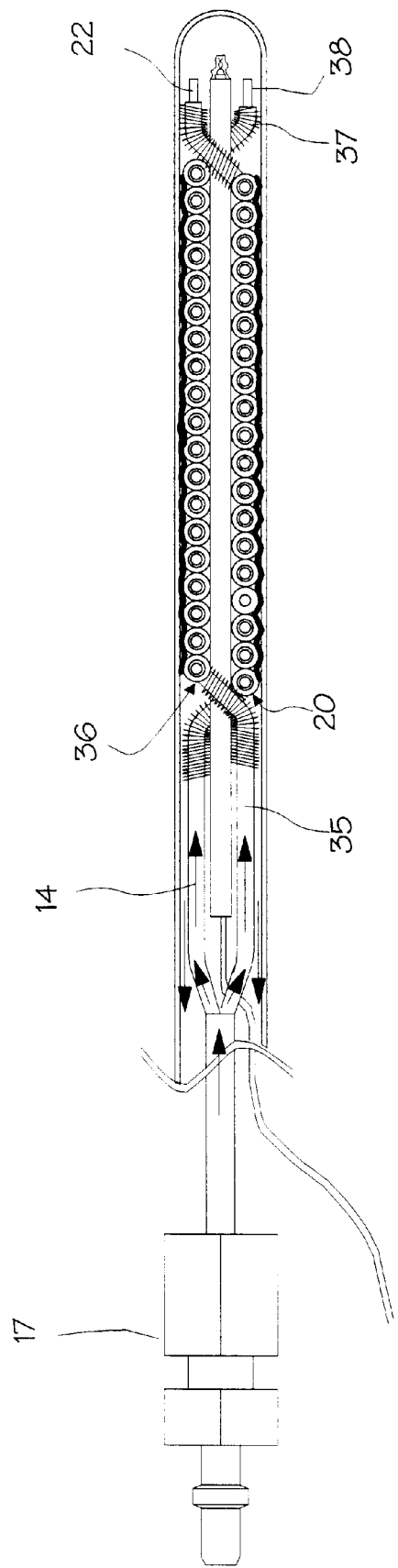
FIG. 8 is a cross section of the cryosurgical probe with parallel fin tubing.
Figure 9:
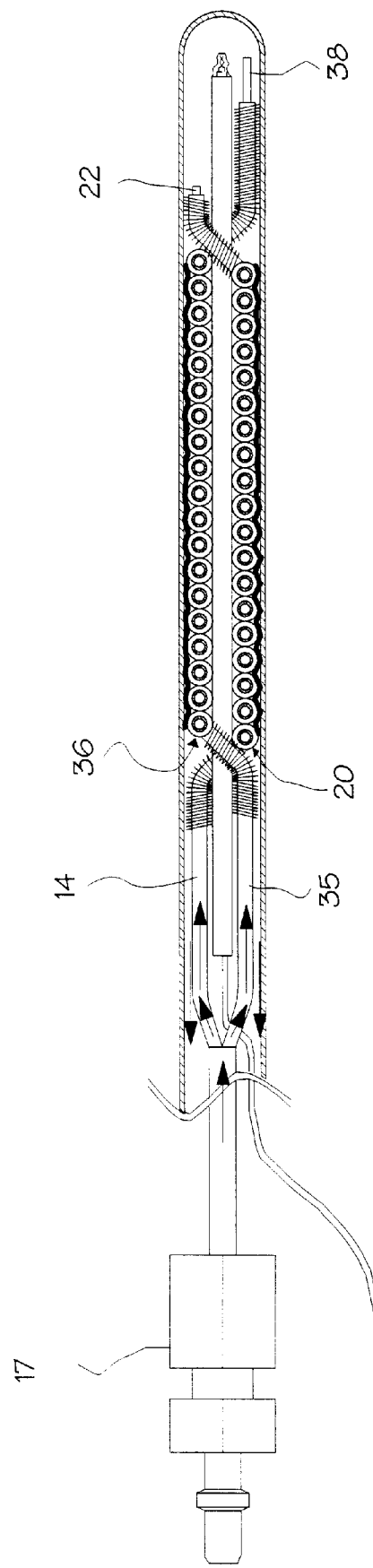
FIG. 9 is a cross section of the cryosurgical probe with parallel fin tubing and offset dual Joule-Thomson nozzles.

FIG. 8 shows a cryosurgical probe which includes two coiled heat exchangers and two Joule-Thomson nozzles. This dual helix cryosurgical probe produces large iceballs. The high pressure gas supply line 14 and finned tube helical coil heat exchanger 20 are the same as those described in reference to the preceding figures. A second high pressure gas supply line 35, heat exchanger 36, gas outlet 37 and Joule-Thomson nozzle 38 are provided. High pressure gas is expanded through both Joule-Thomson nozzles 22 and 38. The helical coils are parallel to each other, meaning that the coils follow the same helical path around the mandrel. When the Joule-Thomson nozzles are located at the same longitudinal location, a large spherical iceball can be formed very rapidly. When the Joule-Thomson nozzles are offset or staggered, meaning that the longitudinal placement of each nozzle is significantly different, the probe very rapidly forms a cylindrical iceball. The cryosurgical probe having two parallel helical coils with gas outlet that are equidistant from the distal tip of the probe is illustrated in FIG. 7. This probe produces a large spherical iceball, and with adjustment of the flow directing sheath can be modified to produce a pear shaped or tear-drop shape. The cryosurgical probe having two parallel helical coils with gas outlets that are offset, with one gas outlet located distal of the other, and thus closer to the distal tip of the probe is illustrated in FIG. 9. This probe with offset Joule-Thomson nozzles produces a large hot dog shaped iceball.

In reference to all the above cryosurgical probes, it is beneficial to have a means for warming the probe quickly. This is desired for therapeutic and practical reasons. Current theory suggests that two cycles of rapid freezing and thawing provides better cryoablation than a single freeze. Practically, it can take a long time for the iceball to thaw so that the probe can be withdrawn from the body. Unless natural thawing is medically indicated, natural thawing is a waste of time.

Prior art warming methods such as exhaust blocking, reverse flow heat transfer, and electrical heating can be employed. The preferred method of warming is to supply high pressure helium gas through the supply line, heat exchanger and Joule-Thomson nozzle. Helium gas is one of the few gases that heat up when expanded through the gas outlet. Thus, the supply of gas to the probes shown in FIGS. 3 through 9 can be switched from high pressure nitrogen or argon to high pressure helium to effect rapid rewarming of the catheter.

Figure 10:
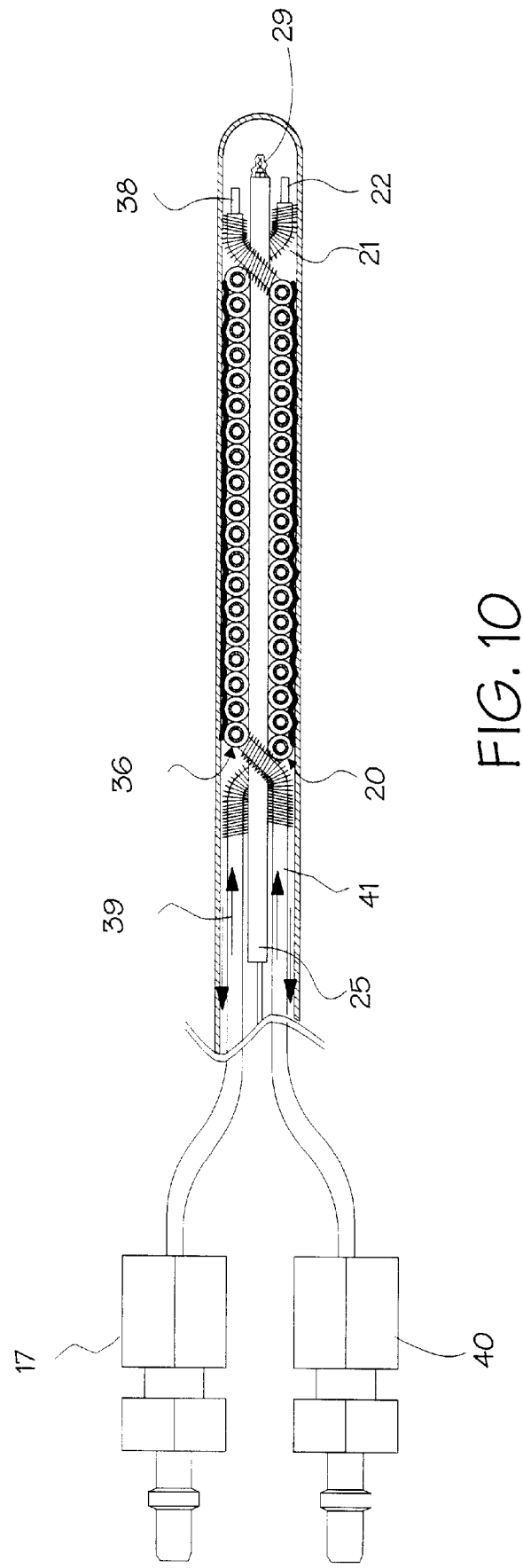
FIG. 10 is a cross section of the cryosurgical probe with parallel fin tubing, adapted for use of one coil for cooling and one coil for heating.

The dual helix embodiment shown in FIGS. 8 and 9 may be modified so that helium may be injected through one supply line aligned only to the helium gas supply, while the other supply line is used only for supply of high pressure cooling gas. This embodiment is shown in FIG. 10, which includes at the proximal end of the flexible tube a high pressure fitting 17 for the cooling gas (nitrogen, argon, $CO_2$, etc.) to the cooling gas supply line 39 and a separate high pressure fitting 40 for helium supply to the warming gas supply line 41. In this embodiment, one supply line, including the heat exchanger 20, gas outlet 21 and Joule-Thomson nozzle 22 is used to cool the probe with a cooling gas, while the second supply line including heat exchanger 36, gas outlet and Joule-Thomson nozzle 38 is used to heat the probe with warming gas. This embodiment is advantageous because the use of the regenerative heat exchanger for the warming gas makes the 5 heating cycle more efficient.

Figure 11:
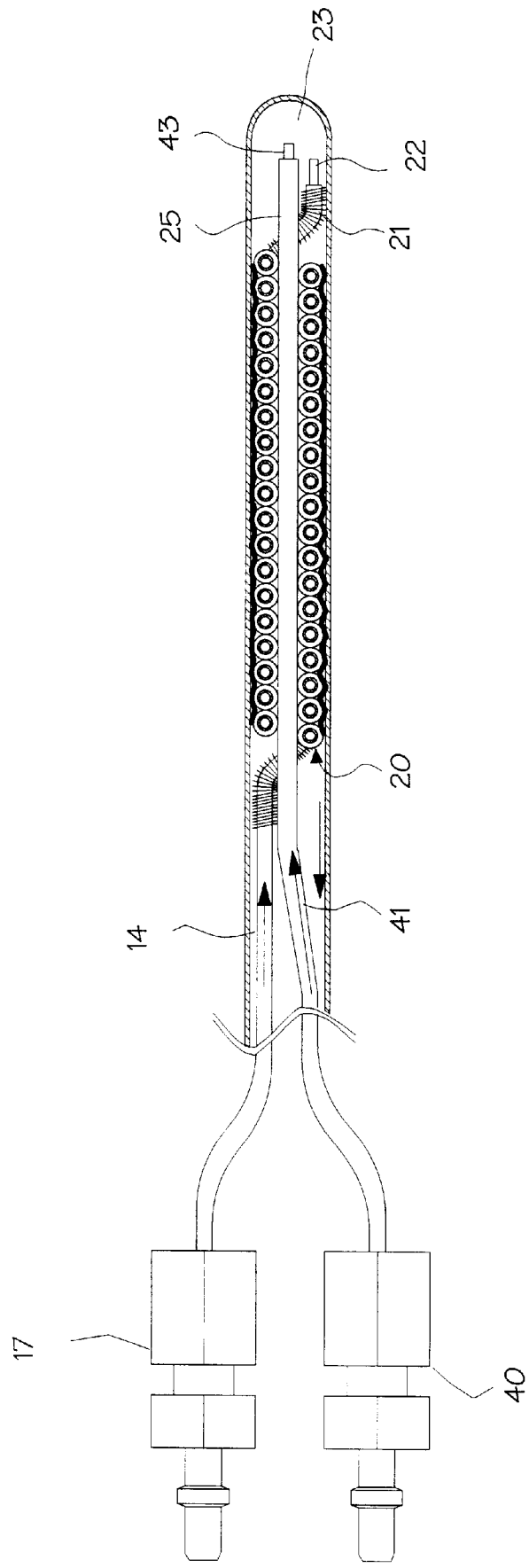
FIG. 11 is a cross section of the cryosurgical probe with a helium Joule-Thomson nozzle.
Figure 12:
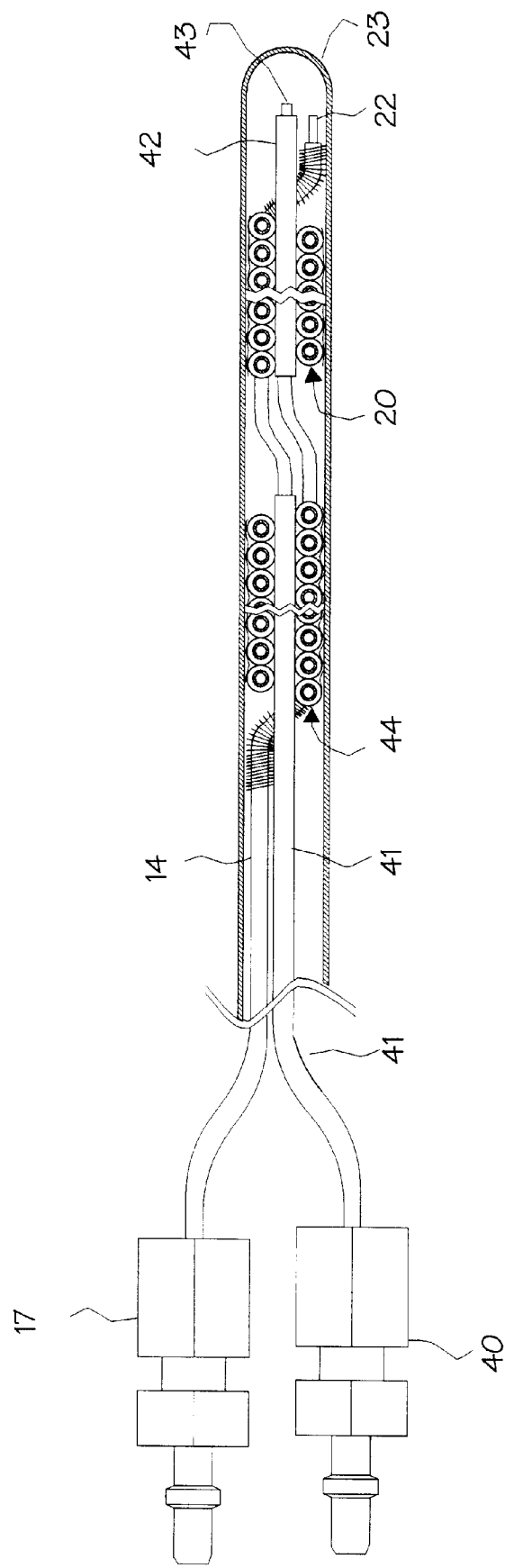
FIG. 12 is a cross section of the cryosurgical probe with longitudinally offset heat exchangers for the cooling and warming gas flow.

In the embodiment shown in FIG. 11, the mandrel 25 also houses a warming gas supply line 41 with a warming gas outlet 42 and Joule-Thomson nozzle 43 injected high pressure heating gas into expansion chamber 23. The warming gas supply line and warming gas outlet extend longitudinally through the center of heat exchanger 20. Helium gas flowing out of the gas outlet into the expansion nozzle gets hotter when in expands and warms the probe. The hot expanded helium then flows proximally over the heat exchanger coils of the cooling gas supply line. However, while heating gas is supplied through heating gas supply line 14, no cooling gas is supplied to the cooling gas supply line. Because no heat exchanger is provided in the warming gas supply line 41, exhausted and hot warming gas does not exchange heat with incoming warming gas that is still at room temperature within the supply line. This is beneficial because the initial blast of warming gas will be cooled well below room temperature by the cryogenic temperature of the probe, and heat exchange of this cold gas with incoming warming gas would lower the temperature of the incoming warming gas and result in slower re-warming. Absence of the heat exchanger in the warming gas supply line thus promotes rapid initial warming of the probe. This may be a concern only for the initial pulse of warming gas. After the exhaust flow has heated the probe to the point where exhausting warming gas is warming the incoming warming gas, a heat exchanger may prove beneficial. Delayed heat exchange may be accomplished by providing the heating gas supply line 41 with a coiled heat exchanger 44 located well proximally of the warming gas outlet 42, as illustrated in FIG. 12. The warming gas heat exchanger 44 is located several inches proximal of the coiled heat exchanger 20 in the cooling gas supply line. The warming gas outlet 42 extends longitudinally through the cooling gas heat exchanger 20. By providing a longitudinally offset heat exchanger for the warming gas supply line, a long initial pulse of warming gas is supplied without heat exchange, but heat exchange is provided in the steady state operation of the warming mode.

Figure 13:
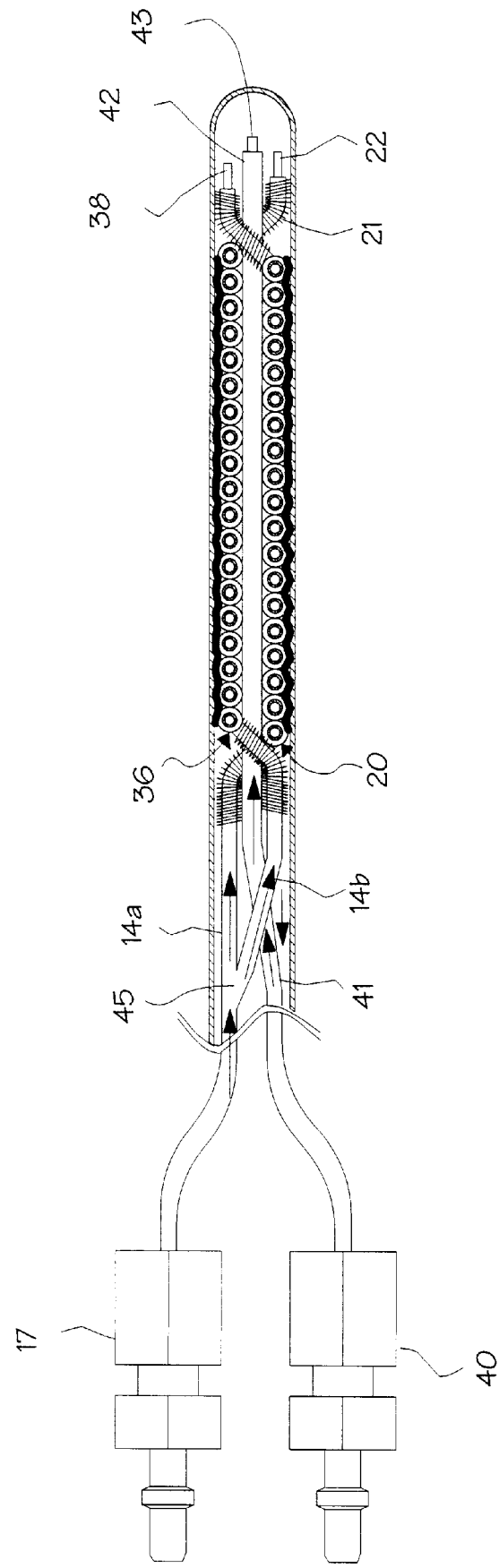
FIG. 13 is a cross section of the cryosurgical probe with parallel fin tubing and a coaxial heating nozzle.
Figure 14:
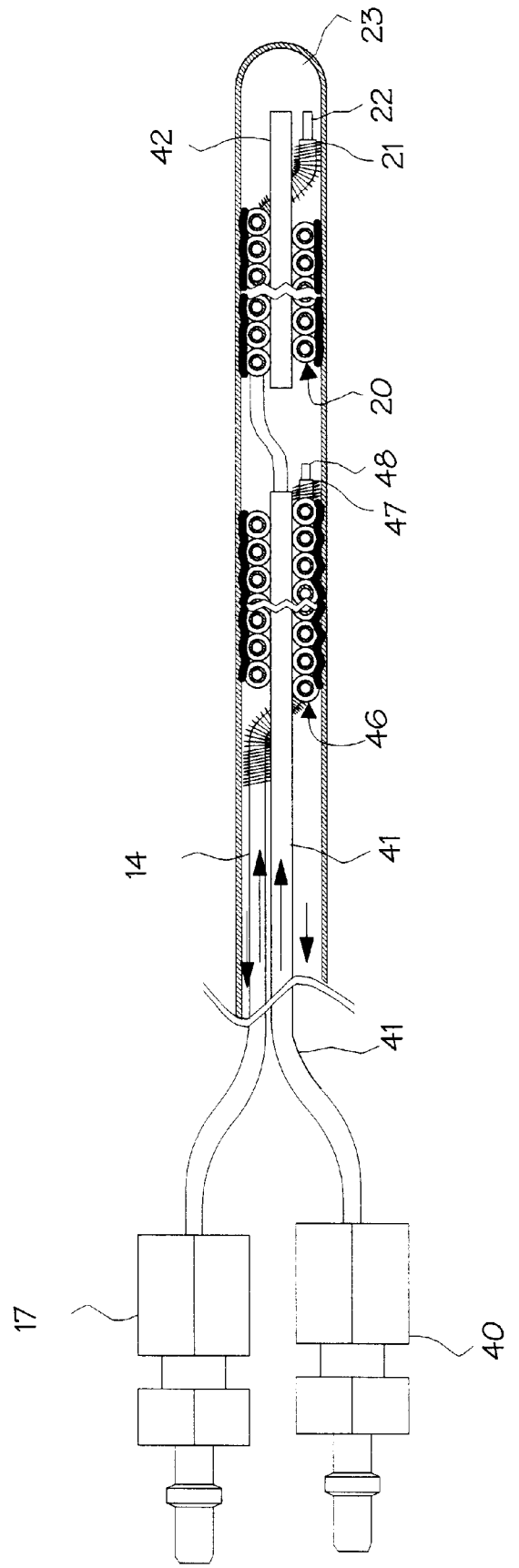
FIG. 14 is a cross section of the cryosurgical probe with longitudinally offset heat exchangers and longitudinally offset Joule-Thomson expansion nozzles.

The cryosurgical probe of FIG. 13 combines the double helix design with the mandrel heating supply line. Cooling gas supply line 39 supplies cooling gas to both helical coils through junction 45 and supply line branches 14a and 14b. Cooling gas is provided through single high pressure fitting 17. The warming gas supply line 41 provides warming gas to the gas outlet 42 and Joule-Thomson nozzle 43 to warm the probe. Thus the large and rapid iceball formation enabled with the probe of FIGS. 8 and 9 is combined with the non-preheated warming flow of FIG. 11. FIG. 14 illustrates another embodiment of a cryosurgical probe which provides cooling flow and warming flow. The heat exchanger 46, gas outlet 47 and Joule-Thomson nozzle 48 in the warming gas supply line is located proximally of the heat exchanger 20, gas outlet 21 and Joule-Thomson nozzle 22 in the cooling gas supply line. This probe facilitates formation of oblong iceballs.

The flow of warming gas can be adjusted and modified. As presented above, the warming gas flow provides heating or warming sufficient to rapidly heat the iceball and melt it. The warming gas flow pathway may be modified to create heating sufficient to cause thermal necrosis of surrounding tissue.

Figure 15:
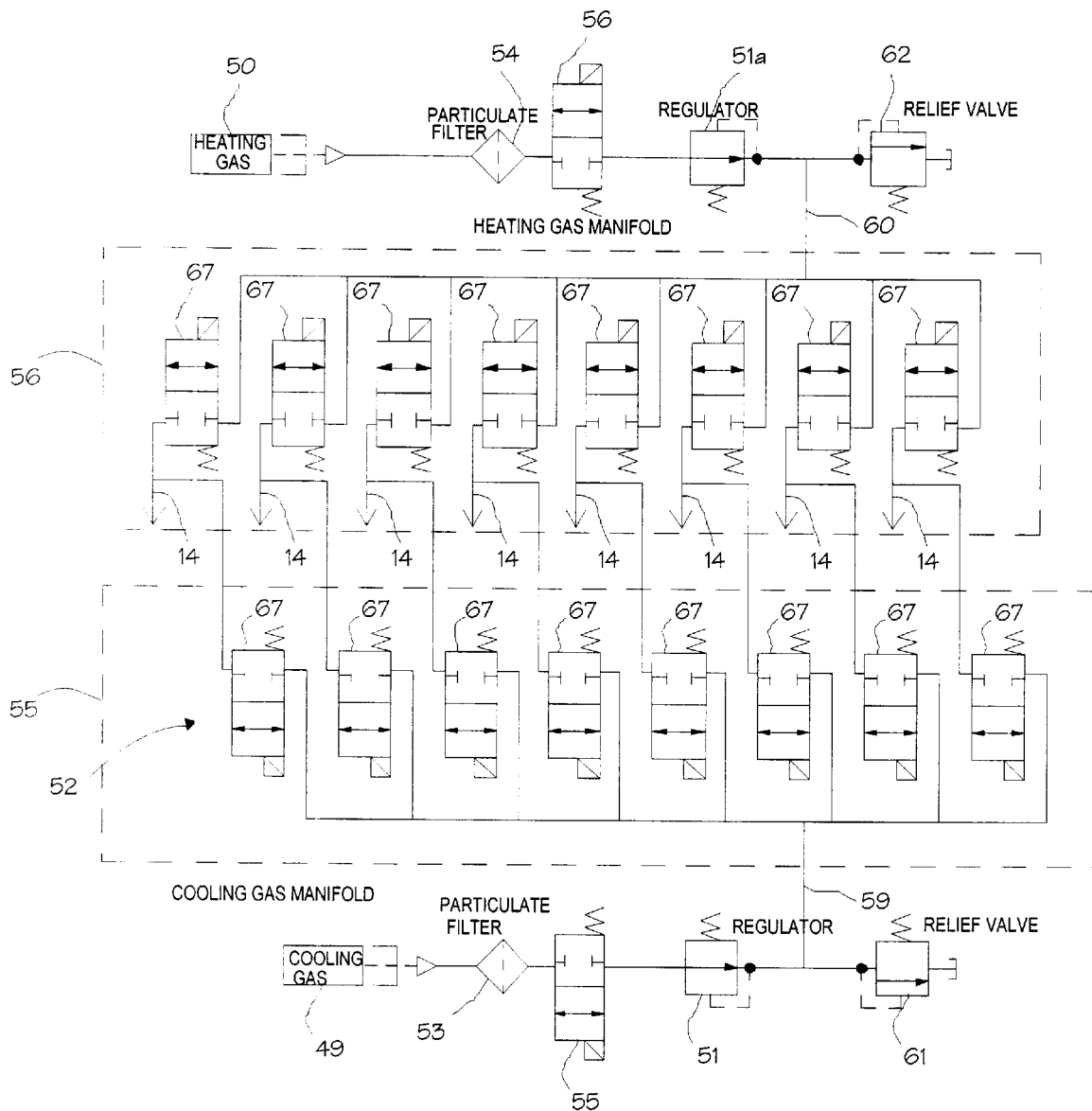
FIGS. 15 and 16 schematics of the manifolds used for 5 operation of the cryosurgical probe.

The gas supply system for the cryoprobes is shown schematically in FIG. 15. High pressure cooling gas is stored in tank 49, and high pressure heating gas is stored in tank 50. Cooling gas such as nitrogen or argon is stored in the flask at 6000 psi and stepped down to about 3200 psi by pressure regulator 51 and supplied to the gas regulating manifold 52. High pressure heating gas (helium) is stored in the flask at 3000 psi and passed through pressure regulator 51a to the gas regulating manifold. Inside the gas regulating manifold, both supply lines are provided with filters 53 and 54 and banks 55 and 56 of solenoid operated cut-off valves. The cooling gas supply line regulator 51 is set at 3000 psi. The heating gas supply line regulator 51a is set at 1000 psi. Both manifold supply lines 59 and 60 are provided with pressure reliefs 61 and 62 and various check valves as needed. Gas is supplied to the appropriate cryosurgical probes in gas dispensing manifolds. The cooling gas dispensing manifold has a manifold of solenoid operated valves 67 for supply of high pressure cooling gas from manifold supply line 59 to the probe supply lines 39. The heating gas manifold of solenoid operated valves 67 supplies high pressure heating gas from the manifold supply line 60 to the various probe supply lines 39. In the preferred cryosurgical control system, eight individual probes are supplied. The probes cool and warm in response to cooling and warming gas through the probes, as controlled by the manifolds. As illustrated, the cooling of each cryosurgical probe in a set of probes can be independently controlled and the warming of each probe in the set of probes can be independently controlled. When the probes make use of a single supply lines such as supply lines 14 indicated in FIG. 15, the dual manifold can be replaced by a series of three way valves which can alternatively connect the probe supply line 14 to the cooling or heating gases.

Figure 16:
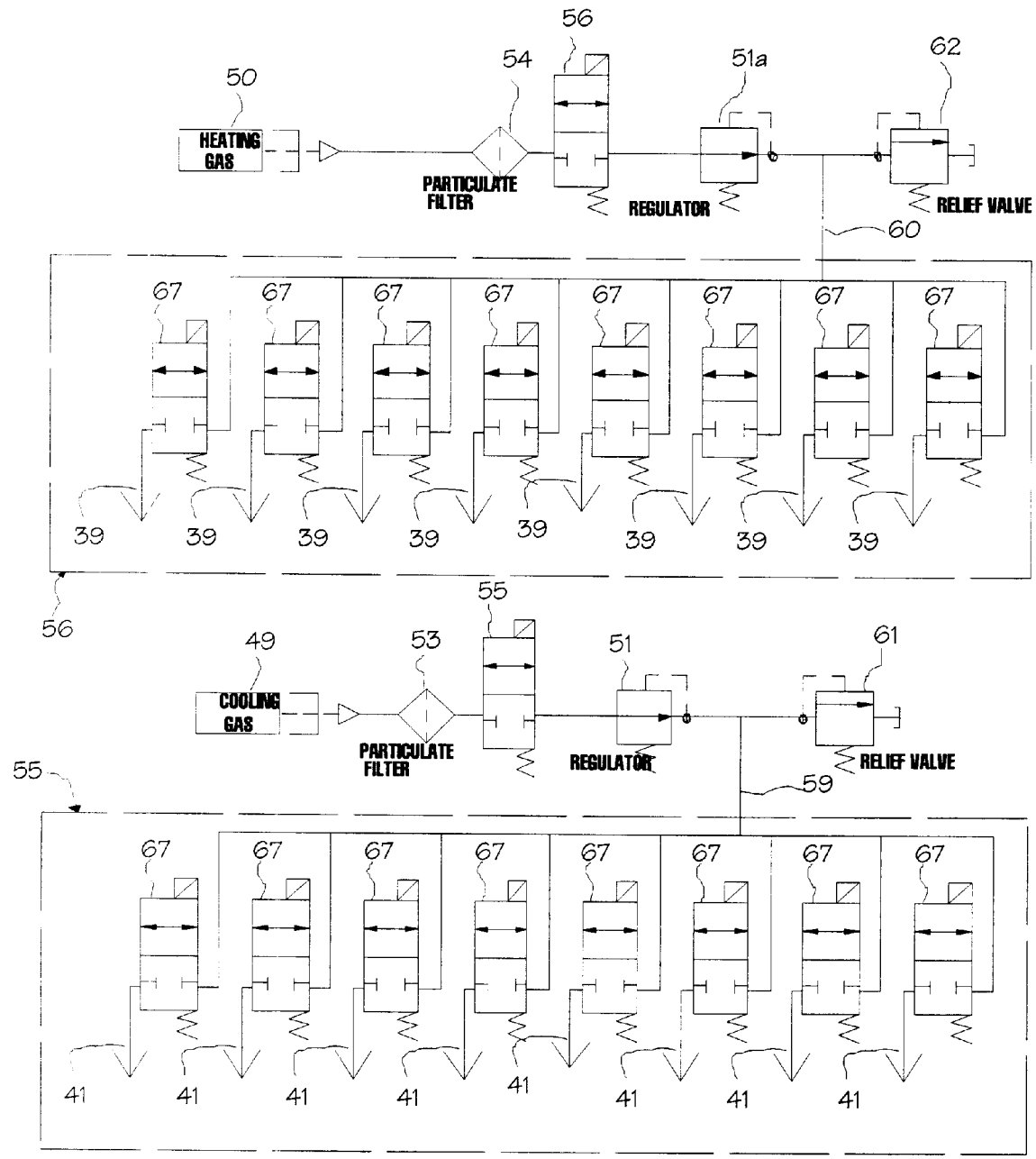

FIG. 16 shows a suitable manifold for independent control of cooling and warming of cryosurgical probes with separate supply lines for cooling and heating gases, such as the probes illustrated in FIGS. 9, 10 and 11. The cooling gas manifold connects the cooling gas manifold supply line to the various probe supply lines 39. The warming gas manifold connects the warming gas supply line to the various probe warming gas supply lines 41. Again, the separate solenoid operated valves may be replaced with combination valves such as four way valves so that a single valve can be used to control flow of cooling gas and warming gas.

In the area of prostate cryoablation, several cryoprobes are used together in a single procedure. In the embodiment illustrated in FIGS. 15 and 16, eight cryoprobes are provided for each procedure. For a variety of reasons, it is beneficial to be able to cool each probe separately, and this feature is provided in current cryoablation systems. During the same procedure, it is also desirable to re-warm the cryosurgical probes independently, to protect anatomic features that seem in danger of freezing (as viewed in the transrectal ultrasound) or to change the position of a probe. The dual manifold illustrated in FIGS. 15 and 16 permit such independent control of the re-warming of the probes.

The gases indicated for use include nitrogen, argon, $NO_2$, and $CO_2$ for use as the cooling gas. These gases are preferred for their ready availability and safety. In theory, any gas which heats up when expanded may be used, and some environments may call for gasses such as oxygen, air, and other gasses. The gas indicated for cooling is preferably helium, but hydrogen and neon are also known to heat up when expanded and may be used in appropriate environments. Hydrogen and oxygen, we expect, will be avoided because their use in most environments will create an unacceptable risk of explosion. The device described above have been developed within the environment of cryosurgery, however the beneficial features will be useful in other environments of use such as electronics cooling and gas testing devices and other areas. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A cryocooler comprising:

A thermally conductive outer sheath having a closed distal end and a chamber within the sheath, said outer sheath being adapted to be inserted into the body of a human patient;

a first coiled heat exchanger comprising a coil of tubing housed within the thermally conductive outer sheath, and disposed coaxially within the outer sheath, said first coiled heat exchanger having a first gas supply line on its proximal end and a first gas outlet on its distal end, said first gas outlet being in fluid communication with the chamber;

a second coiled heat exchanger comprising a coil of tubing housed within the thermally conductive outer sheath, said second coiled heat exchanger being parallel to the first coiled heat exchanger and disposed coaxially within the outer sheath, said second coiled heat exchanger having a second gas supply line on its proximal end and a second gas outlet on its distal end, said second gas outlet being in fluid communication with the chamber.

2. The cryocooler of claim 1 further wherein:

the first gas outlet further comprises a Joule-Thomson nozzle disposed on the first gas outlet; and the second gas outlet further comprises a Joule-Thomson nozzle disposed on the first gas outlet.

3. The cryocooler of claim 1 further wherein:

the first gas outlet communicates into the chamber at a first longitudinal location in relation to the outer sheath; and the second gas outlet communicates into the chamber at a second longitudinal location in relation to the outer sheath, and said second longitudinal location is different from the first longitudinal location.

4. The cryocooler of claim 1 wherein the parallel coaxial coils also have the same diameter.

5. The cryocooler of claim 1 wherein the first gas supply line is connected to a source of cooling gas and the second gas supply line is connected to a source of cooling gas.

6. The cryocooler of claim 1 wherein the first gas supply line is connected to a source of cooling fluid and the second gas supply line is connected to a source of warming fluid.

7. The cryocooler of claim 2 wherein the first gas supply line is connected to a source of cooling gas and the second gas supply line is connected to a source of warming gas.

* * * * *